United States Patent
Dai et al.

(10) Patent No.: US 11,535,583 B1
(45) Date of Patent: Dec. 27, 2022

(54) PREPARATION METHOD OF EICOSAPENTAENOIC ACID ETHYL ESTER

(71) Applicant: Zhejiang Gongshang university, Hangzhou (CN)

(72) Inventors: Zhiyuan Dai, Hangzhou (CN); Pingan Zheng, Hangzhou (CN); Feiyang Zheng, Hangzhou (CN); Yifang Chen, Hangzhou (CN); Jiabin Wang, Hangzhou (CN); Jianlong Zhu, Hangzhou (CN)

(73) Assignee: ZHEJIANG GONGSHANG UNIVERSITY, Hangzhou (CN)

( * ) Notice: Subject to any disclaimer, the term of this patent is extended or adjusted under 35 U.S.C. 154(b) by 0 days.

(21) Appl. No.: 17/568,911

(22) Filed: Jan. 5, 2022

(30) Foreign Application Priority Data

Dec. 3, 2021 (CN) .......................... 202111461791.4

(51) Int. Cl.
    *C07C 67/54*     (2006.01)
    *C11B 3/00*     (2006.01)
    (Continued)

(52) U.S. Cl.
CPC .............. *C07C 67/54* (2013.01); *C07C 67/56* (2013.01); *C07C 69/587* (2013.01); *C11B 3/00* (2013.01); *C11B 3/006* (2013.01); *C11C 3/003* (2013.01)

(58) Field of Classification Search
CPC ....... C07C 67/54; C07C 67/56; C07C 69/587; C11B 3/00; C11B 3/06; C11B 3/006; C11C 1/10; C11C 1/025
See application file for complete search history.

(56) References Cited

U.S. PATENT DOCUMENTS 4,554,107 A * 11/1985 Takao ........................ C11B 3/12
    554/175
9,163,198 B2 * 10/2015 Oroskar .................... C11B 3/02
(Continued)

FOREIGN PATENT DOCUMENTS

| CN | 1263145 A | * | 8/2000 | ............... C11B 3/02 |
| CN | 104846023 A | * | 8/2015 | ............... C12P 7/64 |
| EP | 2914117 B1 | * | 10/2021 | ............... A23D 9/00 |

OTHER PUBLICATIONS

CN104846023, Chen, L. et al., Method for preparing concentrated fish oil fatty acid glyceride, English translation, 9 pages (Year: 2015).*

(Continued)

*Primary Examiner* — Yate' K Cutliff
(74) *Attorney, Agent, or Firm* — WPAT, PC (57) ABSTRACT

A preparation method of eicosapentaenoic acid (EPA) ethyl ester is provided and relates to the field of EPA ethyl ester processing technologies. The preparation method includes: performing degumming and deacidification on a sardine crude oil to obtain a semi-refined sardine oil, performing esterification on the semi-refined sardine oil to obtain an esterified sardine oil and then performing winterization on the esterified sardine oil to thereby obtain an semi-refined esterified sardine oil, performing bleaching and deodorization on the semi-refined esterified sardine oil, and performing multi-stage distillation treatment. Finally, the sardine oil is purified by liquid chromatography to obtain the high purity EPA ethyl ester. The preparation method can improve a utilization rate of the sardine oil and obtain the high-purity EPA ethyl ester.

5 Claims, 3 Drawing Sheets

(51) Int. Cl.
*C07C 69/587* (2006.01)
*C07C 67/56* (2006.01)
*C11C 3/00* (2006.01)

(56) References Cited

U.S. PATENT DOCUMENTS

2002/0111504 A1* 8/2002 Peter .................... C11B 3/06
 554/185
2015/0126760 A1* 5/2015 Doisaki ................. C07C 51/47
 554/175

OTHER PUBLICATIONS

CN1263145, Zhu Huixiang, Process for producing refined fish oil with high polyenoic acid ethyl ester content from crude fish oil, English abstract, 1 page (Year: 2000).*

Ruiz-Mendez, M.V. et al., Oil refining, AOCS lipid library (Year: 2021).*

* cited by examiner

PREPARATION METHOD OF EICOSAPENTAENOIC ACID ETHYL ESTER

TECHNICAL FIELD

The disclosure relates to the field of eicosapentaenoic acid (EPA) ethyl ester processing technologies, and more particularly to a preparation method of EPA ethyl ester.

BACKGROUND

Sardine oil is rich in omega-3 series of polyunsaturated fatty acids (PUFAs), mainly including eicosapentaenoic acid (EPA) and docosahexaenoic acid (DHA). As a "vascular scavenger", EPA can reduce blood cholesterol and triglyceride content, effectively prevent cardiovascular diseases, and has significant effects in the treatment of inflammation, cancer and depression. Therefore, it is widely used in the field of medicine and functional food. However, the EPA content in sardine oil is often less than 30%, which is not as good as medicinal purity.

Because sardine oil contains phospholipids, free fatty acids, cholesterol, pigment and other substances, its physical and chemical indicators do not meet the industry standard of fish oil, so it cannot be used as raw material for preparing high-purity EPA ethyl ester. Generally speaking, before the separation and purification step, fish oil needs a series of treatments, including degumming, deacidification, bleaching, deodorization and esterification. However, when the sardine oil is bleached, activated white clay will adsorb a large amount of fish oil, resulting in low bleaching efficiency, and the high temperature and NaOH addition during the esterification process will make fish oil color reversion. Therefore, it is of great significance to develop efficient and green sardine oil refining methods.

Generally, the separation and purification of fish oil can be divided into non-chromatographic and chromatographic methods. The non-chromatographic methods mainly include low-temperature crystallization, urea inclusion method, molecular distillation method and silver nitrate extraction method; the chromatography methods mainly include silver ion column chromatography, countercurrent chromatography, high performance liquid chromatography and simulated moving bed chromatography. Previous studies have shown that a single method has limited ability to purify EPA, and the combination of multiple methods is a development trend. However, the low-temperature crystallization method involves the use of a large number of toxic reagents, and the silver nitrate extraction involves the use of metal ions, so it is not suitable for industrial production of EPA. At present, the urea inclusion method and the molecular distillation method are the main methods for industrialized production of EPA, but the purity of EPA after the combination of the two methods is usually no more than 80%, and methanol or ethanol may react with urea to produce genotoxic and potentially carcinogenic methyl carbamate or ethyl carbamate.

SUMMARY

In view of the shortcomings of the prior art, the disclosure provides a preparation method of high-purity EPA ethyl ester, aiming to establish a green and efficient preparation method of high-purity EPA and provide reference for industrialized production of EPA.

In order to achieve the above purpose, the disclosure adopts the following technical solution:

a preparation method of high-purity EPA ethyl ester may include the following steps:

step (1), performing degumming and deacidification on a sardine crude oil to obtain a semi-refined sardine oil;

step (2), performing esterification on the semi-refined sardine oil to obtain an esterified sardine oil, and then performing winterization on the esterified sardine oil to thereby obtain a semi-refined esterified sardine oil;

step (3), performing bleaching and deodorization on the semi-refined esterified sardine oil by using vacuum distillation, and collecting heavy phase components and light phase components individually.

step (4), performing a first-stage distillation on the heavy phase components obtained in the step (3) in a molecular distiller with a distillation temperature in a range of 70~80° C. and a distillation pressure of 0.1 Pa, and collecting a first-stage fraction and first-stage heavy phase components;

step (5), performing a second-stage distillation on the first-stage heavy phase components obtained in the step (4) in a molecular distiller with a distillation temperature in a range of 80~90° C. and a distillation pressure of 0.1 Pa, and collecting a second-stage fraction and second-stage heavy phase components;

step (6), performing a third-stage distillation on the second-stage heavy phase components obtained in the step (5) in the molecular distiller with a distillation temperature in a range of 90~100° C. and a distillation pressure of 0.1 Pa, and collecting a third-stage fraction and third-stage heavy phase components; where EPA in the third-stage heavy phase components is greater than 60 wt %; and step (7), purifying the third-stage heavy phase components collected in the step (6) by using a liquid chromatograph to collect a fraction in each of minutes under respective EPA peaks, and removing a solvent of the fraction collected in each of the minutes through vacuum distillation, and combining ones of the fractions collected in the respective minutes having EPA of greater than 95 wt % to thereby obtain the EPA ethyl ester.

In an embodiment, the performing degumming and deacidification on a sardine crude oil in the step (1) specifically includes:

adding phosphoric acid being 1~3% of a weight of the sardine crude oil of into the sardine crude oil, stirring 15~30 minutes at a temperature in a range of 65~85° C. under nitrogen atmosphere and centrifuging to obtain a fish oil in an upper layer; subsequently adding a NaOH aqueous solution with a mass concentration in a range of 10~20% into the fish oil, stirring at a temperature in a range of 65~85° C. for 15~30 minutes under nitrogen atmosphere, centrifuging, and washing with a saturated salt aqueous solution until being neutral; and where an amount of the adding of the NaOH aqueous solution is 1~5% of a weight of the fish oil.

In an embodiment, the performing esterification on the semi-refined sardine oil in the step (2), specifically includes:

weighing a target amount of the semi-refined sardine oil, adding NaOH with 1~3% of a weight of the weighed semi-fined sardine oil of into the weighed semi-refined sardine oil, then dissolving in an absolute ethanol, stirring and refluxing for 30 minutes at a temperature in a range of 65~85° C., and obtaining a fish oil in an upper layer after standing; rinsing the obtained fish oil with a saturated salt aqueous solution until a water layer to be clear/clarified and transparent, then rotating and evaporating the fish oil at 45° C. to remove the ethanol, thereby obtaining the esterified sardine oil; refrigerating the esterified sardine oil at a temperature in a range of 5~15° C. for 4 h, and then removing solid fat from the esterified sardine oil, thereby obtaining the semi-refined esterified sardine oil.

In an embodiment, the performing bleaching and deodorization on the semi-refined esterified sardine oil in the step (3), specifically includes:

placing the semi-refined esterified sardine oil into a feeder for molecular distillation, setting a distillation temperature in a range of 140~160° C., turning on a rotary vane pump and a booster pump sequentially; after a vacuum drops to 0.1 Pa and the distillation temperature reaches a value of the setting, opening an injection inlet, keeping an injection rate at 1~3 mL/min, and keeping a scraper speed in a range of 200~400 r/min; collecting the heavy phase components and the light phase components individually.

In an embodiment, a specification of a chromatographic column of the liquid chromatograph in the step (7) is 150 mm×350 mm, of which a filler is octadecyl bonded silica gel with a particle size of 10 μm. In the step (7), the third-staged heavy phase components collected in the step (6) are dissolved into methanol. A mobile phase is the methanol and water, a volume ratio of the methanol to the water is 95:5~85:15, a flow rate is in a range of 400~800 mL/min, and a detection wavelength is 210 nm.

Compared with the prior art, the embodiments of the disclosure may mainly have the following beneficial effects.

(1) the disclosure bleaches and deodorizes the fish oil through molecular distillation, avoids a large loss of the fish oil after bleaching of traditional white clay, reduces the risk of oil oxidation and avoids the influence of bleaching agents such as white clay on the physical and chemical properties of the fish oil;

(2) the disclosure uses multi-stage molecular distillation to enrich EPA, and selects appropriate distillation temperature, injection flow and scraper speed to control the fatty acid composition in light phase and heavy phase after molecular distillation at all stages, the EPA content in the light phase of the second-stage molecular distillation is equivalent to that of the initial the fish oil, and the EPA content in the light phase of the third-stage molecular distillation is equivalent to that of the heavy phase of the first-stage molecular distillation, it can not only enrich EPA green and efficiently, but also make rational use of fish oil in all stages of light phase, which is helpful to improve the utilization rate of the fish oil; and (3) the preparation of high-purity EPA by chromatography has the advantages of large sample loading and short elution time, and the EPA with purity of 80~99% can be selected according to the demand.

DETAILED DESCRIPTION OF EMBODIMENTS

Figure 1:
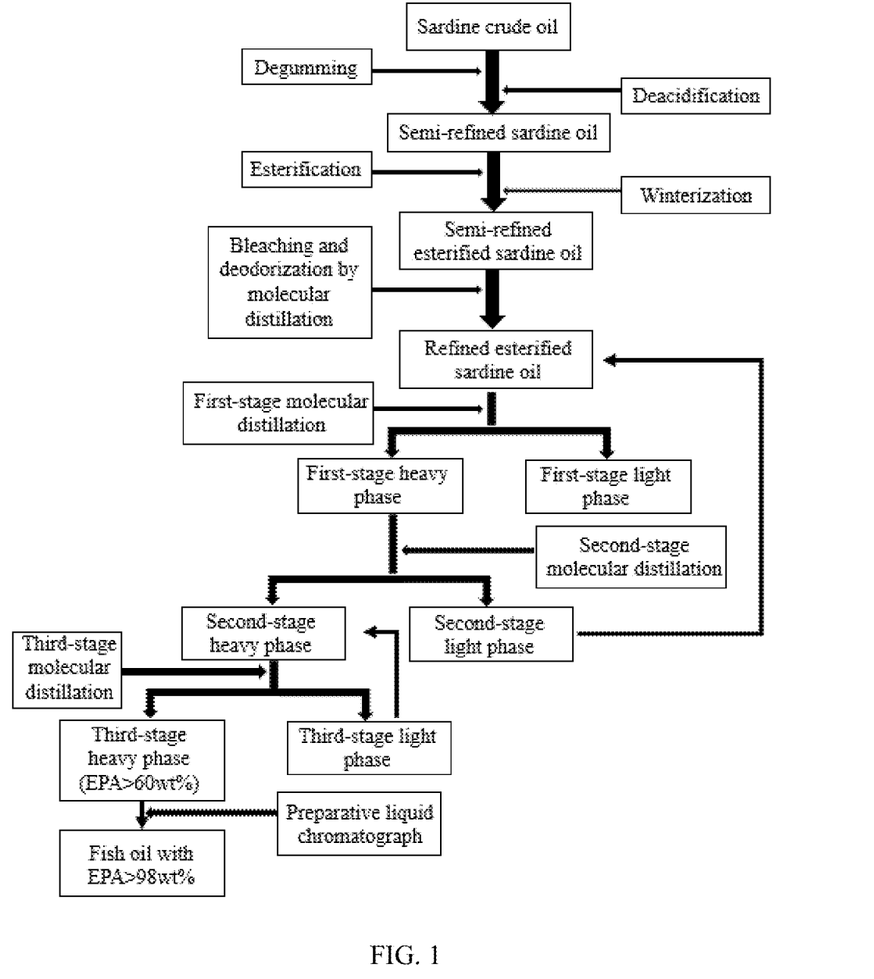
FIG. 1 is a flowchart of a preparation method of eicosapentaenoic acid (EPA) ethyl ester of the disclosure.
Figure 2:
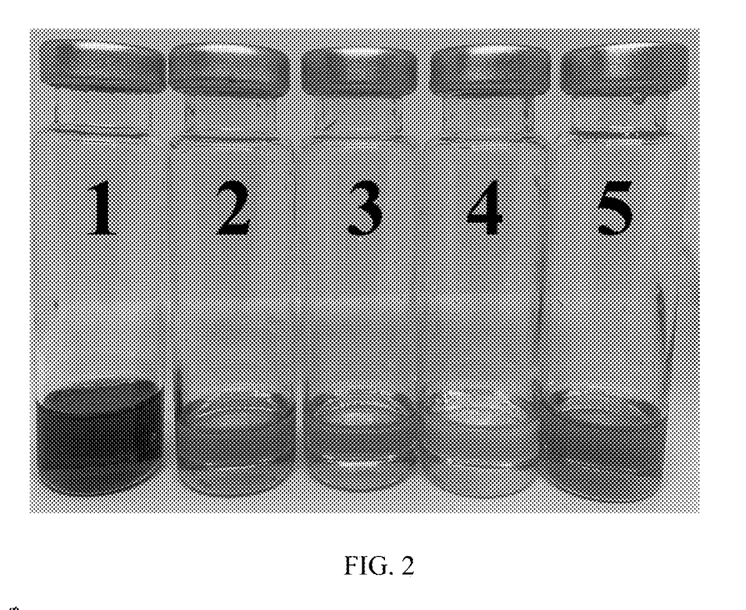
FIG. 2 is a physical map of a color change of a sardine oil in a refining process of disclosure, where bottle 1 contains a sardine crude oil, bottle 2 contains a degummed and deacidified sardine oil (also referred to as a semi-refined sardine oil), bottle 3 contains a clay bleached sardine oil, bottle 4 contains a molecular distilled sardine oil, and bottle 5 contains an esterified sardine oil.
Figure 3:
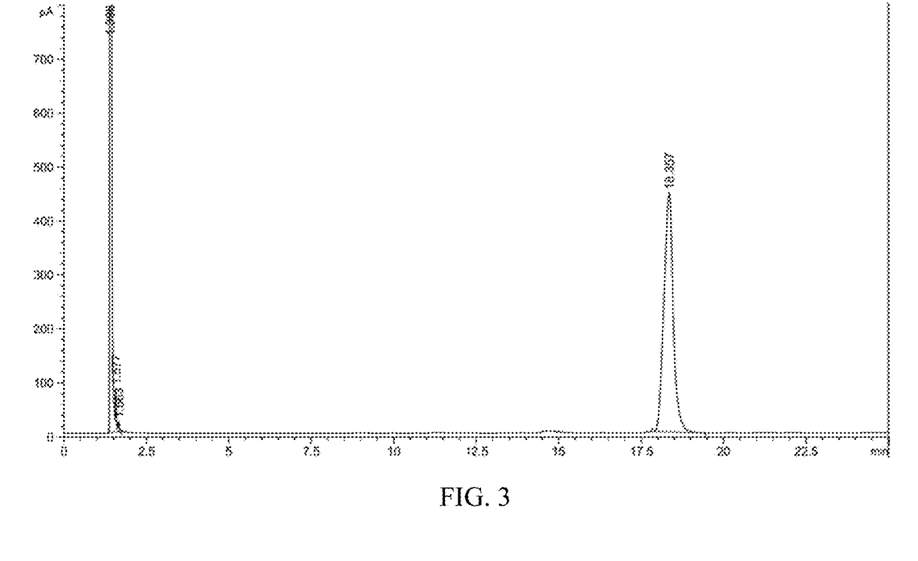
FIG. 3 is a gas phase diagram of a high purity eicosapentaenoic acid ethyl ester (EPA-EE) of the disclosure.
Figure 4:
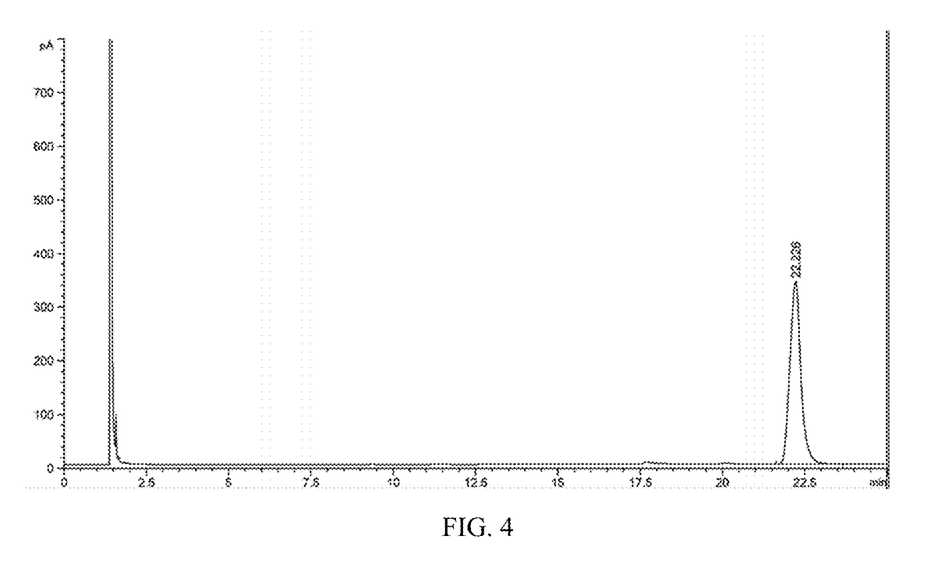
FIG. 4 is a gas phase diagram of a high purity docosahexaenoic acid ethyl ester (DHA-EE) of the disclosure.

The disclosure is further described below in combination with specific embodiments.

Embodiment 1

Step (1), degumming and deacidification of sardine crude oil, which specifically includes: 3% of a weight of the sardine crude oil of phosphoric acid are added into 100 grams (g) of the sardine crude oil, stirred at 85 degrees Celsius (° C.) for 30 minutes under nitrogen atmosphere and centrifuged to obtain 88.35 g of degummed fish oil in an upper layer. A mass concentration of 20% of sodium hydroxide (NaOH) aqueous solution are added into 100 g of the degummed fish oil, and an adding amount of the NaOH aqueous solution is 1% of a weight of the degummed fish oil. The degummed fish oil mixed the NaOH aqueous solution is stirred at 85° C. for 30 minutes under nitrogen atmosphere and centrifuged, and rinsed with a saturated salt aqueous solution until being neutral, thereby obtaining 92.62 g of deacidified fish oil (also referred to as semi-refined sardine oil).

Step (2), esterification and winterization of the semi-refined sardine oil, which specifically includes: 3 g of NaOH are added into 100 g of the semi-refined sardine oil, mixed with 60 g of absolute ethanol, and then stirred and refluxed for 30 minutes at 85° C. After being placed, the esterified fish oil in an upper layer is taken and rinsed with the saturated salt aqueous solution until a water layer became clear/clarified and transparent. Subsequently, the rinsed fish oil is distilled through vacuum distillation at 45° C. to remove ethanol, thereby obtaining 96.64 g of esterified sardine oil. 100 g of the esterified sardine oil are refrigerated at 5° C. for 4 hours (h), solid fat in the esterified sardine oil is removed, thereby obtaining 92.98 g of semi-refined esterified sardine oil.

Step (3), vacuum distillation of the semi-refined esterified sardine oil, which specifically includes: a molecular distillation equipment (also referred to as molecular distiller) is turned on, and 200 g of the semi-refined esterified sardine oil are placed into a feeder of the molecular distiller. A distillation temperature is set at 160° C., then a rotary vane pump and a booster pump are turned on sequentially. When the vacuum drops to 0.1 pascals (Pa) and the distillation temperature reaches the set value, an injection inlet is opened, an injection rate is kept at 1 milliliter per minute (mL/min), and a scraper speed is kept at 400 revolutions per minute (r/min); and 12.37 g of heavy phase components and 184.22 g of light phase components are collected individually.

Step (4), first-stage distillation of the heavy phase components, which specifically includes: the molecular distiller is turned on, and 200 g of the heavy phase components collected in the step (3) are placed into the molecular distiller for first-stage distillation. A distillation temperature is set at 80° C., the rotary vane pump and the booster pump are turned on sequentially. After the vacuum drops to 0.1 Pa and the distillation temperature reaches the set value, the injection inlet is opened, the injection flow rate is kept at 1 mL/min and the scraper speed is kept at 400 r/min. The first-stage heavy phase components and the first-stage light phase components (also referred to as first-stage fraction) are collected individually, in which the contents of eicosapentaenoic acid (EPA) and docosahexaenoic acid (DHA) in the first-stage heavy phase are 37.50% and 8.32% respectively and the contents of EPA and DHA in the first-stage light phase are 8.53% and 2.33% respectively.

Step (5), second-stage distillation of the first-stage heavy phase components, which specifically includes: fish oil of the first-stage heavy phase components collected in the step (4) is placed into the molecular distiller for second-stage distillation. The distillation temperature is set at 90° C., the rotary vane pump and the booster pump are turned on sequentially. After the vacuum drops to 0.1 Pa and the distillation temperature reaches the set value, the injection inlet is opened, the injection flow rate is kept at 1 mL/min and the scraper speed at 400 r/min. The second-stage heavy phase components and the second-stage light phase components (also referred to as second-stage fraction) are collected individually, in which the contents of EPA and DHA in the second-stage heavy phase are 52.81% and 12.72% respectively and the contents of EPA and DHA in the second-stage light phase are 18.79% and 7.34% respectively.

Step (6), third-stage distillation of the second-stage heavy phase components, which specifically includes: fish oil of the second-stage heavy phase components collected in the step (5) is placed into the molecular distiller for third-stage distillation. The distillation temperature is set at 100° C., the rotary vane pump and the booster pump are turned on sequentially. After the vacuum drops to 0.1 Pa and the distillation temperature reaches the set value, the injection inlet is opened, the injection flow rate is kept at 1 mL/min and the scraper speed is kept at 500 r/min. The third-stage heavy phase components and the third-stage light phase components (also referred to as third-stage fraction) are collected individually, in which the contents of EPA and DHA in the third-stage heavy phase are 63.29% and 18.22% respectively and the contents of EPA and DHA in the third-stage light phase are 53.86% and 11.28% respectively.

step (7), purification of the third-stage heavy phase component, which specifically includes: a dynamic axial compression column device (DAC-150 device) is selected to prepare high-purity EPA, in which the specification of DAC column is 150 millimeters (mm)×350 mm, of which the filler is octadecyl bonded silica gel with a particle size of 10 micrometers (μm), 10 g of fish oil of the third-stage heavy phase collected in the step (6) are dissolved into methanol. A mobile phase is methanol and water, (a volume ratio of the methanol to the water is 85:15), a flow rate is 800 mL/min, and a detection wavelength is 210 nanometers (nm). The fraction in each of minutes under respective EPA peaks is collected, the solvent of the fraction collected in each of the minutes is removed through vacuum distillation, ones of the fractions collected in the respective minutes having EPA of greater than 95 wt % are combined, and finally EPA with a purity greater than 98% is obtained. In addition, the molecular distiller used in the step (3), the molecular distiller used in the step (4), the molecular distiller used in the step (5) and the molecular distiller used in the step (6) can be the same molecular distiller or different molecular distillers.

Embodiment 2

Step (1), degumming and deacidification of sardine crude oil, which specifically includes: 1% of a weight of the sardine crude oil of phosphoric acid are added into 100 g of the sardine crude oil, stirred for 15 minutes at 65° C. under nitrogen atmosphere and centrifuged to obtain 90.32 g of degummed fish oil in an upper layer. A mass concentration of 10% of NaOH aqueous solution are added into 100 g of the degummed fish oil, and an adding amount of the NaOH aqueous solution is 1% of a weight of the degummed fish oil. The degummed fish oil mixed the NaOH aqueous solution is stirred at 65° C. for 15 minutes under nitrogen atmosphere and centrifuged, and rinsed with a saturated salt aqueous solution until being neutral, thereby obtaining 93.77 g of deacidified fish oil (also referred to as semi-refined sardine oil).

Step (2), esterification and winterization of the semi-refined sardine oil, which specifically includes: 3 g of NaOH are added into 100 g of the semi-refined sardine oil, mixed with 60 g of absolute ethanol, and then stirred and refluxed for 30 minutes at 65° C. After being placed, the esterified fish oil in an upper layer is taken and rinsed with the saturated salt aqueous solution until a water layer became clear and transparent. Subsequently, the rinsed fish oil is distilled through vacuum distillation at 45° C. to remove ethanol, thereby obtaining 95.52 g of esterified sardine oil. 100 g of the esterified sardine oil are refrigerated at 15° C. for 4 h, solid fat in the esterified sardine oil is removed, thereby obtaining 97.86 g of semi-refined esterified sardine oil.

Step (3), vacuum distillation of the semi-refined esterified sardine oil, which specifically includes: a molecular distiller is turned on, and 200 g of the semi-refined esterified sardine oil are placed into a feeder of the molecular distiller). A distillation temperature is set at 140° C., then a rotary vane pump and a booster pump are turned on sequentially. When the vacuum drops to 0.1 Pa and the distillation temperature reaches the set value, an injection inlet is opened, an injection rate is kept at 4 mL/min, and a scraper speed is kept at 200 r/min; and 17.69 g of heavy phase components and 179.41 g of light phase components are collected individually.

Step (4), first-stage distillation of the heavy phase components, which specifically includes: the molecular distiller is turned on, and 200 g of the heavy phase components obtained in the step (3) are placed into the molecular distiller for first-stage distillation. A distillation temperature is set at 70° C., the rotary vane pump and the booster pump are turned on sequentially. After the vacuum drops to 0.1 Pa and the distillation temperature reaches the set value, the injection inlet is opened, the injection flow rate is kept at 3 mL/min and the scraper speed is kept at 200 r/min. The first-stage heavy phase components and the first-stage light phase components are collected individually, in which the contents of EPA and DHA in the first-stage heavy phase are 34.13% and 8.54% respectively and the contents of EPA and DHA in the first-stage light phase are 7.12% and 5.06% respectively.

Step (5), second-stage distillation of the first-stage heavy phase components, which specifically includes: fish oil of the first-stage heavy phase components collected in the step (4) is placed into the molecular distiller for second-stage distillation. The distillation temperature is set at 80° C., the rotary vane pump and the booster pump are turned on sequentially. After the vacuum drops to 0.1 Pa and the distillation temperature reaches the set value, the injection inlet is opened, the injection flow rate is kept at 3 mL/min and the scraper speed at 200 r/min. The second-stage heavy phase components and the second-stage light phase components are collected individually, in which the contents of EPA and DHA in the second-stage heavy phase are 48.51% and 12.22% respectively and the contents of EPA and DHA in the second-stage light phase are 15.47% and 4.40% respectively.

Step (6), third-stage distillation of the second-stage heavy phase components, which specifically includes: 200 g of fish oil of the second-stage heavy phase components collected in the step (5) are placed into the molecular distiller for third-stage distillation. The distillation temperature is set at 90° C., the rotary vane pump and the booster pump are turned on sequentially. After the vacuum drops to 0.1 Pa and the distillation temperature reaches the set value, the injection inlet is opened, the injection flow rate is kept at 4 mL/min and the scraper speed is kept at 300 r/min. The third-stage heavy phase components and the third-stage light phase components are collected individually, in which the contents of EPA and DHA in the third-stage heavy phase are 60.06% and 18.01% respectively and the contents of EPA and DHA in the third-stage light phase are 48.41% and 12.43% respectively.

Step (7), purification of the third-stage heavy phase components, which specifically includes: a dynamic axial compression column device (DAC-150 device) is selected to prepare high-purity EPA, in which the specification of DAC column is 150 mm×250 mm, of which the filler isoctadecyl bonded silica gel with a particle size of 10 μm, 10 g of fish oil of the third-stage heavy phase collected in the step (6) are dissolved into methanol. A mobile phase is methanol and water, (a volume ratio of the methanol to the water is 95:5), a flow rate is 400 mL/min, and a detection wavelength is 210 nm. The fraction in each of minutes under respective EPA peaks is collected, the solvent of the fraction collected in each of the minutes is removed through vacuum distillation, ones of the fractions collected in the respective minutes having EPA of greater than 95 wt % are combined, and finally EPA with a purity greater than 98% is obtained.

Embodiment 3

Step (1), degumming and deacidification of sardine crude oil, which specifically includes: 2% of a weight of the sardine crude oil of phosphoric acid are added into 100 g of sardine crude oil, stirred for 25 minutes at 75° C. under nitrogen atmosphere and centrifuged to obtain 90.15 g of degummed fish oil in an upper layer. A mass concentration of 15% of NaOH aqueous solution are added into 100 g of the degummed fish oil, and an adding amount of the NaOH aqueous solution is 3% of a weight of the degummed fish oil. The degummed fish oil mixed the NaOH aqueous solution is stirred at 75° C. for 20 minutes under nitrogen atmosphere and centrifuged, and rinsed with a saturated salt aqueous solution until being neutral, thereby obtaining 93.77 g of deacidified fish oil (also referred to as semi-refined sardine oil).

Step (2), esterification and winterization of the semi-refined sardine oil, which specifically includes: 2 g of NaOH are added into 100 g of the semi-refined sardine oil, mixed with 60 g of absolute ethanol, and then stirred and refluxed for 25 minutes at 70° C. After being placed, the esterified fish oil in an upper layer is taken and rinsed with the saturated salt aqueous solution until a water layer became clear and transparent. Subsequently, the rinsed fish oil is distilled through vacuum distillation at 45° C. to remove ethanol, thereby obtaining 95.52 g of esterified sardine oil. 100 g of the esterified sardine oil are refrigerated at 10° C. for 4 h, solid fat in the esterified sardine oil is removed, thereby obtaining 95.86 g of semi-refined esterified sardine oil.

Step (3), vacuum distillation of the semi-refined esterified sardine oil, which specifically includes: a molecular distiller is turned on, and 200 g of the semi-refined esterified sardine oil are placed into a feeder of the molecular distiller. A distillation temperature is set at 150° C., then a rotary vane pump and a booster pump are turned on sequentially. When the vacuum drops to 0.1 Pa and the distillation temperature reaches the set value, an injection inlet is opened, an injection rate is kept at 2 mL/min, and a scraper speed is kept at 300 r/min; and 12.69 g of heavy phase components and 179.41 g of light phase components are collected individually.

Step (4), first-stage distillation of the heavy phase components, which specifically includes: the molecular distiller is turned on, and 200 g of the heavy phase components collected in the step (3) are placed into the molecular distiller for first-stage distillation. A distillation temperature is set at 75° C., the rotary vane pump and the booster pump are turned on sequentially. After the vacuum drops to 0.1 Pa and the distillation temperature reaches the set value, the injection inlet is opened, the injection flow rate is kept at 2 mL/min and the scraper speed is kept at 300 r/min. The first-stage heavy phase components and the first-stage light phase components are collected individually, in which the contents of EPA and DHA in the first-stage heavy phase are 36.81% and 9.38% respectively and the contents of EPA and DHA in the first-stage light phase are 7.95% and 5.42% respectively.

Step (5), second-stage distillation of the first-stage heavy phase components, which specifically includes: fish oil of the first-stage heavy phase components collected in the step (4) are placed into the molecular distiller for second-stage distillation. The distillation temperature is set at 85° C., the rotary vane pump and the booster pump are turned on sequentially. After the vacuum drops to 0.1 Pa and the distillation temperature reaches the set value, the injection inlet is opened, the injection flow rate is kept at 2 mL/min and the scraper speed at 300 r/min. The second-stage heavy phase components and the second-stage light phase components are collected individually, in which the contents of EPA and DHA in the second-stage heavy phase are 50.13% and 11.94% respectively and the contents of EPA and DHA in the second-stage light phase are 19.79% and 10.22% respectively. The content of fatty acids in the second-stage light phase is similar to the initial fish oil, so it can be incorporated into the initial fish oil.

Step (6), third-stage distillation of the second-stage heavy phase components, which specifically includes: 200 g of fish oil of the second-stage heavy phase components collected in the step (5) are placed into the molecular distiller for third-stage distillation. The distillation temperature is set at 100° C., the rotary vane pump and the booster pump are turned on sequentially. After the vacuum drops to 0.1 Pa and the distillation temperature reaches the set value, the injection inlet is opened, the injection flow rate is kept at 3 mL/min and the scraper speed is kept at 400 r/min. The third-stage heavy phase components and the third-stage light phase components are collected individually, in which the contents of EPA and DHA in the third-stage heavy phase are 61.82% and 19.78% respectively and the contents of EPA and DHA in the third-stage light phase are 51.97% and 11.08% respectively.

step (7), purification of the third-stage heavy phase components, which specifically includes: a dynamic axial compression column device (DAC-150 device) is selected to prepare high-purity EPA, in which the specification of DAC column is 150 mm×350 mm, of which the filler is octadecyl bonded silica gel with a particle size of 10 μm, 7 g of fish oil of the third-stage heavy phase collected in the step (6) are dissolved into methanol. A mobile phase is methanol and water, (a volume ratio of the methanol to the water is 92:8), a flow rate is 500 mL/min, and a detection wavelength is 210 nm. The fraction in each of minutes under respective EPA peaks is collected, the solvent of the fraction collected in each of the minutes is removed through vacuum distillation, ones of the fractions collected in the respective minutes having EPA of greater than 95 wt % are combined, and finally EPA with a purity greater than 98% is obtained.

Comparison Embodiment 1

Step (1), 2% of a weight of sardine crude oil of phosphoric acid are added into 100 g of the sardine crude oil, stirred for 25 minutes at 75° C. under nitrogen atmosphere and centrifuged to obtain 90.15 g of degummed fish oil in an upper layer. A mass concentration of 15% of NaOH aqueous solution are added into 100 g of the degummed fish oil, and an adding amount of the NaOH aqueous solution is 3% of a weight of the degummed fish oil. The degummed fish oil mixed the NaOH aqueous solution is stirred at 75° C. for 20 minutes under nitrogen atmosphere and centrifuged, and rinsed with a saturated salt aqueous solution until being neutral, thereby obtaining 93.77 g of deacidified fish oil.

Step (2), 2 g of NaOH are added into 100 g of the semi-refined sardine oil, mixed with 60 g of absolute ethanol, and then stirred and refluxed for 25 minutes at 70° C. After being placed, the esterified fish oil in an upper layer is taken and rinsed with the saturated salt aqueous solution until a water layer became clear and transparent. Subsequently, the rinsed fish oil is distilled through vacuum distillation at 45° C. to remove ethanol, thereby obtaining 95.52 g of esterified sardine oil. 100 g of the esterified sardine oil are refrigerated at 10° C. for 4 h, solid fat in the esterified sardine oil is removed, thereby obtaining 95.86 g of semi-refined esterified sardine oil.

Step (3), 10% of a weight of the semi-refined esterified sardine oil of active white clay are added into 100 g of the semi-refined esterified sardine oil, stirred at 85° C. for 30 minutes under nitrogen atmosphere and centrifuged to obtain 91.72 g of bleached fish oil in an upper layer. 100 g of the bleached fish oil are deodorized by rotary evaporation at 120° C. for 4 h to obtain 98.30 g of deodorized fish oil.

Steps (4)-(7) are respectively same as the steps (4)-(7) of the embodiment 3.

Comparison Embodiment 2

Step (1), 2% of a weight of sardine crude oil of phosphoric acid are added into 100 g of the sardine crude oil, stirred for 25 minutes at 75° C. under nitrogen atmosphere and centrifuged to obtain 89.77 g of degummed fish oil in an upper layer. A mass concentration of 15% of NaOH aqueous solution are added into 100 g of the degummed fish oil, and an adding amount of the NaOH aqueous solution is 3% of a weight of the degummed fish oil. The degummed fish oil mixed the NaOH aqueous solution is stirred at 75° C. for 20 minutes under nitrogen atmosphere and centrifuged, and rinsed with a saturated salt aqueous solution until being neutral, thereby obtaining 94.15 g of deacidified fish oil.

Step (2), 10% of a weight of the deacidified fish oil of active white clay are added into 100 g of the deacidified fish oil, stirred at 85° C. for 30 minutes under nitrogen atmosphere and centrifuged to obtain 90.56 g of bleached fish oil in an upper layer. 100 g of the bleached fish oil are deodorized by rotary evaporation at 120° C. for 4 h to obtain 98.79 g of deodorized fish oil.

Step (3), 2 g of NaOH are added into 100 g of the deodorized fish oil, mixed with 40 g of absolute ethanol, and then stirred and refluxed for 25 minutes at 70° C. After being placed, the esterified fish oil in an upper layer is taken and rinsed with the saturated salt aqueous solution until a water layer became clear and transparent. Subsequently, the rinsed fish oil is distilled through vacuum distillation at 45° C. to remove ethanol, thereby obtaining 96.37 g of esterified sardine oil. 100 g of the esterified sardine oil are refrigerated at 10° C. for 4 h, solid fat in the esterified sardine oil is removed, thereby obtaining 95.44 g of semi-refined esterified sardine oil.

Steps (4)-(7) are respectively same as the steps (4)-(7) of the embodiment 3.

Comparison Embodiment 3

Step (1), 1% of a weight of sardine crude oil of phosphoric acid are added into 100 g of the sardine crude oil, stirred for 15 minutes at 85° C. under nitrogen atmosphere and centrifuged to obtain 88.56 g of degummed fish oil in an upper layer. A mass concentration of 20% of NaOH aqueous solution are added into 100 g of the degummed fish oil, and an adding amount of the NaOH aqueous solution is 1% of a weight of the degummed fish oil. The degummed fish oil mixed the NaOH aqueous solution is stirred at 85° C. for 15 minutes under nitrogen atmosphere and centrifuged, and rinsed with a saturated salt aqueous solution until being neutral, thereby obtaining 91.78 g of deacidified fish oil (also referred to as semi-refined sardine oil).

Step (2), 3 g of NaOH are added into 100 g of the semi-refined sardine oil, mixed with 60 g of absolute ethanol, and then stirred and refluxed for 30 minutes at 85° C. After being placed, the esterified fish oil in an upper layer is taken and rinsed with the saturated salt aqueous solution until a water layer became clear and transparent. Subsequently, the rinsed fish oil is distilled through vacuum distillation at 45° C. to remove ethanol, thereby obtaining 96.76 g of esterified sardine oil. 100 g of the esterified sardine oil are refrigerated at 5° C. for 4 h, solid fat in the esterified sardine oil is removed, thereby obtaining 92.17 g of semi-refined esterified sardine oil.

Step (3), a molecular distiller is turned on, and 200 g of the semi-refined esterified sardine oil are placed into a feeder of the molecular distiller. A distillation temperature is set at 160° C., then a rotary vane pump and a booster pump are turned on sequentially. When the vacuum drops to 0.1 Pa and the distillation temperature reaches the set value, an injection inlet is opened, an injection rate is kept at 1 mL/min, and a scraper speed is kept at 200 r/min; and 10.84 g of heavy phase components and 187.96 g of light phase components are collected individually.

Step (4), the molecular distiller is turned on, and 200 g of the heavy phase components collected in the step (3) are placed into the molecular distiller for first-stage distillation. A distillation temperature is set at 100° C., the rotary vane pump and the booster pump are turned on sequentially. After the vacuum drops to 0.1 Pa and the distillation temperature reaches the set value, the injection inlet is opened, the injection flow rate is kept at 1 mL/min and the scraper speed is kept at 400 r/min. The first-stage heavy phase components and the first-stage light phase components are collected individually, in which the contents of EPA and DHA in the first-stage heavy phase are 48.12% and 14.54% respectively and the contents of EPA and DHA in the first-stage light phase are 14.28% and 8.96% respectively.

Step (5), a dynamic axial compression column device (DAC-150 device) is selected to prepare high-purity EPA, in which the specification of DAC column is 150 mm×250 mm, of which the filler is octadecyl bonded silica gel with a particle size of 10 μm, 10 g of fish oil of the first-stage heavy phase collected in the step (4) are dissolved into methanol. A mobile phase is methanol and water, (a volume ratio of the methanol to the water is 85:15), a flow rate is 800 mL/min, and a detection wavelength is 210 nm. The fraction in each of minutes under respective EPA peaks is collected, the solvent of the fraction collected in each of the minutes is removed through vacuum distillation, ones of the fractions collected in the respective minutes having EPA of greater than 95 wt % are combined, and finally EPA with a purity greater than 98% is obtained.

Comparison Embodiment 4

Step (1), 1% of a weight of the sardine crude oil of phosphoric acid are added into 100 g of sardine crude oil, stirred for 15 minutes at 65° C. under nitrogen atmosphere and centrifuged to obtain 90.63 g of degummed fish oil in an upper layer. A mass concentration of 10% of NaOH aqueous solution are added into 100 g of the degummed fish oil, and an adding amount of the NaOH aqueous solution is 1% of a weight of the degummed fish oil. The degummed fish oil mixed the NaOH aqueous solution is stirred at 65° C. for 15 minutes under nitrogen atmosphere and centrifuged, and rinsed with a saturated salt aqueous solution until being neutral, thereby obtaining 94.21 g of deacidified fish oil (also referred to as semi-refined sardine oil).

Step (2), 3 g of NaOH are added into 100 g of the semi-refined sardine oil, mixed with 60 g of absolute ethanol, and then stirred and refluxed for 30 minutes at 65° C. After being placed, the esterified fish oil in an upper layer is taken and rinsed with the saturated salt aqueous solution until a water layer became clear and transparent. Subsequently, the rinsed fish oil is distilled through vacuum distillation at 45° C. to remove ethanol, thereby obtaining 94.64 g of esterified sardine oil. 100 g of the esterified sardine oil are refrigerated at 15° C. for 4 h, solid fat in the esterified sardine oil is removed, thereby obtaining 97.27 g of semi-refined esterified sardine oil.

Step (3), a molecular distiller is turned on, and 200 g of the semi-refined esterified sardine oil are placed into a feeder of the molecular distiller. A distillation temperature is set at 140° C., then a rotary vane pump and a booster pump are turned on sequentially. When the vacuum drops to 0.1 Pa and the distillation temperature reaches the set value, an injection inlet is opened, an injection rate is kept at 4 mL/min, and a scraper speed is kept at 200 r/min; and 15.11 g of heavy phase components and 180.09 g of light phase components are collected individually.

Step (4), the molecular distiller is turned on, and 200 g of the heavy phase components obtained in the step (3) are placed into the molecular distiller for first-stage distillation. A distillation temperature is set at 70° C., the rotary vane pump and the booster pump are turned on sequentially. After the vacuum drops to 0.1 Pa and the distillation temperature reaches the set value, the injection inlet is opened, the injection flow rate is kept at 3 mL/min and the scraper speed is kept at 200 r/min. The first-stage heavy phase components and the first-stage light phase components are collected individually, in which the contents of EPA and DHA in the first-stage heavy phase are 35.63% and 8.74% respectively and the contents of EPA and DHA in the first-stage light phase are 7.92% and 5.45% respectively.

Step (5), 200 g of fish oil of the first-stage heavy phase components collected in the step (4) are placed into the molecular distiller for second-stage distillation. The distillation temperature is set at 80° C., the rotary vane pump and the booster pump are turned on sequentially. After the vacuum drops to 0.1 Pa and the distillation temperature reaches the set value, the injection inlet is opened, the injection flow rate is kept at 3 mL/min and the scraper speed at 200 r/min. The second-stage heavy phase components and the second-stage light phase components are collected individually, in which the contents of EPA and DHA in the second-stage heavy phase are 48.38% and 11.72% respectively and the contents of EPA and DHA in the second-stage light phase are 17.47% and 5.30% respectively. The content of fatty acids in the second-stage light phase is similar to the initial fish oil, so it can be incorporated into the initial fish oil.

Step (6), 200 g of fish oil of the second-stage heavy phase components collected in the step (5) is placed into the molecular distiller for third-stage distillation. The distillation temperature is set at 90° C., the rotary vane pump and the booster pump are turned on sequentially. After the vacuum drops to 0.1 Pa and the distillation temperature reaches the set value, the injection inlet is opened, the injection flow rate is kept at 4 mL/min and the scraper speed is kept at 300 r/min. The third-stage heavy phase components and the third-stage light phase components are collected individually, in which the contents of EPA and DHA in the third-stage heavy phase are 61.35% and 18.53% respectively and the contents of EPA and DHA in the third-stage light phase are 49.26% and 11.07% respectively.

Step (7), a dynamic axial compression column device (DAC-150 device) is selected to prepare high-purity EPA, in which the specification of DAC column is 150 mm×350 mm, of which the filler is octadecyl bonded silica gel with a particle size of 10 μm, 10 g of fish oil of the third-stage heavy phase obtained in the step (6) are dissolved into methanol. A mobile phase is methanol, a flow rate is 400 mL/min, and a detection wavelength is 210 nm. The fraction in each of minutes under respective EPA peaks is collected, the solvent of the fraction collected in each of the minutes is removed through vacuum distillation, ones of the fractions collected in the respective minutes having EPA of greater than 95 wt % are combined, and finally EPA with a purity greater than 98% is obtained.

The above are only the illustrated embodiments of the disclosure, but the protection scope of the disclosure is not limited to this. Those skilled in the related art can easily think of changes or replacements within the technical scope disclosed by the disclosure, which should be covered by the protection scope of the disclosure. Therefore, the protection scope of the disclosure shall be subject to the protection scope of the claims.

What is claimed is:

1. A preparation method of eicosapentaenoic acid (EPA) ethyl ester, comprising:
    step (1), performing degumming and deacidification on a sardine crude oil to obtain a semi-refined sardine oil;
    step (2), performing esterification on the semi-refined sardine oil to obtain an esterified sardine oil, and then performing winterization on the esterified sardine oil to thereby obtain a semi-refined esterified sardine oil;
    step (3), performing bleaching and deodorization on the semi-refined esterified sardine oil by vacuum distillation, and collecting heavy phase components and light phase components individually;
    step (4), performing a first-stage distillation on the heavy phase components obtained in the step (3) in a molecular distiller with a distillation temperature in a range of 70~80 degrees Celsius (° C.) and a distillation pressure of 0.1 pascals (Pa), and collecting a first-stage fraction and first-stage heavy phase components;
    step (5), performing a second-stage distillation on the first-stage heavy phase components obtained in the step (4) in a molecular distiller with a distillation temperature in a range of 80~90° C. and a distillation pressure of 0.1 Pa, and collecting a second-stage fraction and second-stage heavy phase components;

step (6), performing a third-stage distillation on the second-stage heavy phase components obtained in the step (5) in a molecular distiller with a distillation temperature in a range of 90~100° C. and a distillation pressure of 0.1 Pa, and collecting a third-stage fraction and third-stage heavy phase components, wherein EPA in the third-stage heavy phase components is greater than 60 wt %; and step (7), purifying the third-stage heavy phase components collected in the step (6) by using a liquid chromatograph to collect a fraction in each of minutes under respective EPA peaks, removing a solvent of the fraction collected in each of the minutes through vacuum distillation, and combining ones of the fractions collected in the respective minutes having EPA of greater than 95 wt % to thereby obtain the EPA ethyl ester.

2. The preparation method according to claim 1, wherein the performing degumming and deacidification on a sardine crude oil in the step (1) specifically comprises:

adding phosphoric acid being 1~3% of a weight of the sardine crude oil into the sardine crude oil, stirring 15~30 minutes at a temperature in a range of 65~85° C. under nitrogen atmosphere and centrifuging to obtain a fish oil in an upper layer; and subsequently adding a sodium hydroxide (NaOH) aqueous solution with a mass concentration in a range of 10~20% into the fish oil, stirring for 15~30 minutes at a temperature in a range of 65~85° C. under nitrogen atmosphere, centrifuging, and rinsing with a saturated salt aqueous solution until being neutral;

wherein an amount of the adding of the NaOH aqueous solution is 1~5% of a weight of the fish oil.

3. The preparation method according to claim 1, wherein the performing esterification on the semi-refined sardine oil in the step (2) specifically comprises:

weighing a target amount of the semi-refined sardine oil, adding NaOH with 1~3% of a weight of the weighed semi-fined sardine oil into the weighed semi-refined sardine oil, then dissolving in an absolute ethanol, stirring and refluxing for 30 minutes at a temperature in a range of 65~85° C., and obtaining a fish oil in an upper layer after standing;

rinsing the obtained fish oil with a saturated salt aqueous solution until a water layer to be clear and transparent, then rotating and evaporating the fish oil at 45° C. to remove the ethanol, thereby obtaining the esterified sardine oil; and refrigerating the esterified sardine oil at a temperature in a range of 5~15° C. for 4 hours (h), and then removing solid fat from the esterified sardine oil, thereby obtaining the semi-refined esterified sardine oil.

4. The preparation method according to claim 1, wherein the performing bleaching and deodorization on the semi-refined esterified sardine oil in the step (3) specifically comprises:

placing the semi-refined esterified sardine oil into a feeder for molecular distillation, setting a distillation temperature in a range of 140~160° C., turning on a rotary vane pump and a booster pump sequentially;

after a vacuum drops to 0.1 Pa and the distillation temperature reaches a value of the setting, opening an injection inlet, keeping an injection rate at 1~3 milliliters per minute (mL/min), and keeping a scraper speed in a range of 200~400 revolutions per minute (r/min); and collecting the heavy phase components and the light phase component individually.

5. The preparation method according to claim 1, wherein a specification of a chromatographic column of the liquid chromatograph in the step (7) is 150 millimeters (mm)×350 mm, of which a filler is octadecyl bonded silica gel with a particle size of 10 micrometers (μm);

wherein in the step (7), the third-stage heavy phase components collected in the step (6) are dissolved into methanol, a mobile phase is the methanol and water, a volume ratio of the methanol to the water is in a range of 95:5~85:15, a flow rate is in a range of 400~800 mL/min, and a detection wavelength is 210 nanometers (nm).

* * * * *